United States Patent [19]

Okada

[11] Patent Number: 4,687,470

[45] Date of Patent: Aug. 18, 1987

[54] CATHETER FOR NASOGASTRIC INTUBATION

[75] Inventor: Yosuke Okada, Tokyo, Japan

[73] Assignee: Sherwood Medical Company, St. Louis, Mo.

[21] Appl. No.: 809,534

[22] Filed: Dec. 16, 1985

[51] Int. Cl.⁴ ............................................. A61M 25/02
[52] U.S. Cl. .................................... 604/171; 604/163; 604/161; 604/270; 604/285; 128/657; 128/DIG. 26
[58] Field of Search ............... 604/163, 171, 161, 270, 604/285, 275; 128/657, DIG. 26

[56] References Cited

U.S. PATENT DOCUMENTS

| Re. 31,855 | 3/1985 | Osborne | 604/161 |
| 3,853,130 | 12/1974 | Sheridan | 604/171 |
| 4,175,564 | 11/1979 | Kwak | 604/171 |
| 4,411,654 | 10/1983 | Boarini et al. | 604/161 |
| 4,412,832 | 11/1983 | Kling et al. | 604/161 |
| 4,480,639 | 11/1984 | Peterson et al. | 128/DIG. 26 |
| 4,576,589 | 3/1986 | Kraus et al. | 604/161 |

Primary Examiner—C. Fred Rosenbaum
Assistant Examiner—John D. Ferros
Attorney, Agent, or Firm—Stanley N. Garber; Andrew J. Beck; Charles E. Smith

[57] ABSTRACT

The present invention provides an intubation assembly for nasogastric intubation comprising a catheter and a plastic sheath tube for encasing the catheter along substantially the full length thereof, the sheath tube having a longitudinal tear-off line over the full length thereof and having elasticity and rigidity slightly greater than the catheter which is slidably inserted in the sheath tube.

2 Claims, 3 Drawing Figures

4,687,470

CATHETER FOR NASOGASTRIC INTUBATION

BACKGROUND OF THE INVENTION

The present invention relates to a catheter for nasogastric intubation.

Normally, a catheter for nasogastric intubation to be used for nutritional purposes comprises a weighted portion in which a weight is sealed into a distal end of a soft small-diameter plastic tube. The weighted portion is inserted through a nostril into the esophagous and into the stomach or the intestines, the weight facilitating catheter placement for supply of a nutritious liquid through one or two side holes positioned slightly above the weighted portion.

Since the catheter remains positioned in and through the nostril for a long period of time, a patient may feel considerable pain. To avoid such pain, the catheter is preferably formed of a material as soft as possible. Moreover, since the catheter remains in contact with the walls of the internal organs for a long period of time, if the catheter is formed of a hard material, the tissue of the walls of the internal organs may be injured Also, for this reason, it is desired that the catheter be formed from a soft plastic tube. However, any such tube has to be inserted into the stomach and intestines following a tortuous path through the nostril, the narrow-passage larynx, and the esophagus and therefore a catheter made of a soft plastic tube lacks the requisite stiffness and is therefore difficult to insert.

In the past, therefore, a method has been employed in which a guide wire is inserted into the bore of the catheter to increase the catheter stiffness. In this procedure, however, insertion of the guide wire into the catheter required that a lubricant be used to coat the internal surfaces of the bore of the catheter to decrease the frictional resistance therebetween. Such procedure is unnecessarily time-consuming, and in addition, insertion of the guide wire is cumbersome.

Furthermore, the procedure may result in projection of the the end of the guide wire through one of the side holes of the catheter where it may pierce the walls of the internal organs.

BRIEF DESCRIPTION OF THE INVENTION

DETAILED DESCRIPTION OF THE INVENTION

This invention overcome the disadvantages as noted above. Procedurally, a catheter 1 according to the present invention is inserted and encased into a plastic insertion guide or sheath tube 3 having at least one longitudinal tear-off line 4 over the full length thereof and having elasticity and rigidity slightly greater than those of the catheter 1, the sheath tube 3 and the catheter 4 are then inserted together into the patient's stomach or the intestines. With this arrangement, the sheath tube 3 and catheter 1 can be extremely easily inserted through the nostril into the intestines and/or the stomach, and after insertion, the sheath tube 3 is withdrawn and by longitudinally tearing-off the sheath tube 3 externally of the nostril, the sheath tube is removed with the result that only the catheter 1 remains positioned within the patient's intestines and/or stomach. Further, the tearing-off of the sheath tube 3 may be carried out extremely easily by a tube fixing means B secured externally of the nostril.

Figure 1:
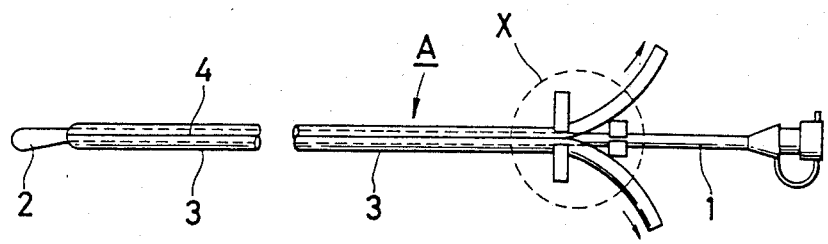
FIG. 1 is an explanatory view of a catheter for insertion through the patients nose according to the present invention.
Figure 2:
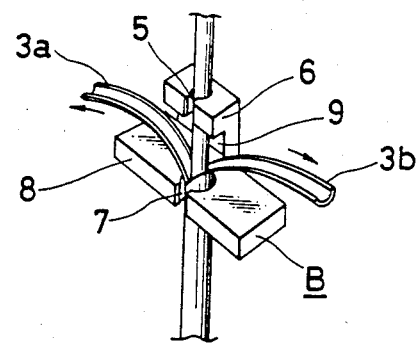
FIG. 2 is an enlarged explanatory view showing a portion of the catheter of FIG. 1 designated "X" in FIG. 1.

The catheter 1 according to the present invention is shown in FIG. 1. the catheter 1 is constructed of very soft material and is provided at its distal end with a weighted portion 2, and a side hole (not shown) is provided slightly above the weighted portion 2 for feeding a nutrituous liquid. The plastic sheath tube 3, which slidably receives the catheter 1 therein, has an elasticity and rigidity slightly greater than that of the catheter and is adapted to be torn away by separation along a longitudinal tear-off line 4 extending over the full length of the tube. The tear-off line 4 has less wall thickness than that of other portions of the tube and/or may be formed from other weaker material than the remainder of the tube.

The assembled intubation assembly A for nasogastric intubation (which comprises the catheter 1 encased in the sheath tube 3) further includes a catheter fixing means B positioned on the proximal end of the tube assembly 3.

Figure 3:
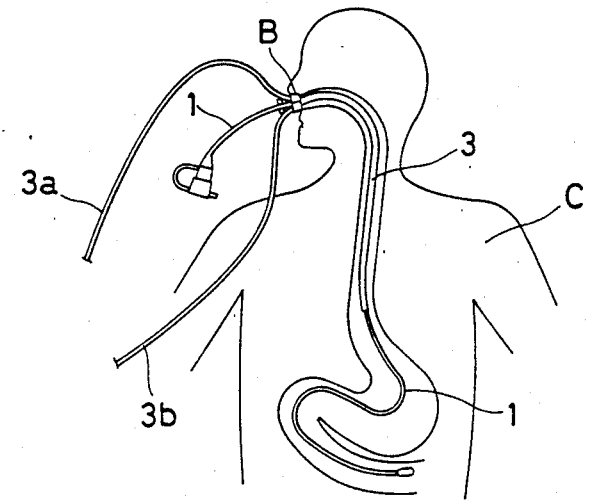
FIG. 3 is an schematic view showing a catheter according to the present invention inserted through the patient's nose into the patient's stomach and small intestine.

The fixing means B is formed from a somewhat thick plastic plate, in "C"-shaped form which comprises an outwardly disposed catheter pinching plate 6 having a key-shaped catheter pinching groove 5 for pinching and frictionally engaging the catheter and an outer, tube support plate 8 having a sheath tube supporting key-shaped groove 7 for softly or loosely supporting the sheath tube 3 encasing the catheter 1. The plates 6 and 8 are positioned parallel to each other at a small spaced relation. The sheath tube 3 maybe torn off into two parts (3a, 3b) along longitudinal tear-off lines 4 (two tear-off lines in the illustrated embodiment) in a space between the catheter pinching plate 6 and the sheath tube support plate 8. Only the catheter 1 is positively pinched in the catheter pinching groove 5. The end of the sheath tube 3 may be withdrawn from the patient easily whereby it may be removed from the assembly and only the cathether 1 remains with its distal end inserted into the stomach and intestines. However, in the assembled condition the tube assembly A, insertion of the catheter into the stomach and intestines may be easily carried out. FIG. 3 shows the state where the distal end of the catheter 1 has been directed through the pylorus into the small intestine, and the sheath tube 3 is partially withdrawn from the patient by tearing the tube 3 into two parts 3a and 3b by means of the tear-off lines 4 between the pinching and support plates 6 and 8 of the fixing means B externally of the nostril. The distal end of the sheath tube 3 is moved upward to the point that the sheath tube may be removed completely and only the catheter 1 remains positively pinched and fixed at the pinching groove 5 of the pinching plate 6. Reference character C designates the human body.

In accordance with the present invention, the catheter is slidably encased by the sheath tube over substantially the full length of the catheter, and the insertion of the catheter formed from a soft plastic tube into the nostril, and stomach and intestines may be carried out extremely easily and safely. The catheter of the invention is more convenient to use as compared with the prior art catheters and greatly reduces pain and danger to the patient.

It is to be noted that the catheter 1 according to the present invention even if not provided with a weighted portion at the distal end thereof, can be inserted into the sheath tube 3 and the tube assembly A conveniently inserted into the stomach and intestines. This results from the adequate elasticity and rigidity of the sheath tube, and even if the sheath tube is raised or withdrawn while being torn off as previously mentioned, the catheter will not be withdrawn with the sheath tube. To assist in withdrawal of the tube 3 without disturbing an unweighted catheter the inner walls of the sheath tube or the outer surface of the catheter may be made smooth to decrease the sliding resistance or such withdrawal facilitated by using the lubricant. It will be also noted that two tear-off lines of the sheath tube are not always required but even a single line can be used to achieve the intended objective.

This sheath tube can be removed from the catheter without using the fixing means B in such a manner that the distal end of the sheath tube is moved upward and withdrawn by tearing it off by hands. In this case, however, two persons are required, one person firmly holding the catheter in position while the other performs the tearing-off work.

In accordance with the present invention, it is preferred that the aforementioned fixing means B be used, and therefore, one person will suffice to effect his operation. Since the catheter 1 is firmed pinched and fixed at the pinching groove 5 of the catheter pinching plate 6, the tearing-off operation can be performed by a single person, thus providing for an extreme convenience. Labor-saving results may be achieved by utilization of the inexpensive fixing means B according to the present invention.

What is claimed is:

1. A medical intubation assembly a distal end of which is adapted to be inserted internally of a patient, said assembly comprising
   a relatively soft catheter of a first relatively small diameter and having a length to reach from externally of the patient to a desired point internally of the patient;
   a relatively rigid longitudinally splittable insertion tube of a second and relatively larger diameter and having an internal bore slidably receiving and encasing said catheter, said insertion tube having, and being splittable along, two opposed longitudinally extending lines of weakness along the full length thereof to facilitate splitting thereof for withdrawal from the patient and removal from about said catheter; and
   a catheter fixing means adapted to be removably fixed adjacent a proximal end of said catheter externally of the patient for fixedly positioning said catheter during withdrawal of said insertion tube from the patient and removal of said insertion tube from about said catheter, said catheter fixing means including a plate means adapted to abut the patient adjacent the location of insertion of the intubation assembly, the catheter fixing means including a catheter receiving groove having a diameter slightly smaller than said first diameter for pinching engagement with said catheter during withdrawal and removal of said insertion tube from about said catheter, portions of said plate means positioned on opposite sides of said groove to abut each of the split halves of said insertion tube upon withdrawal thereof to assist in separating and splitting of said insertion tube along said longitudinally extending lines.

2. A nasogastric intubation assembly a distal end of which is adapted to be inserted through a patient's nostril and esophagus into the patient's intestine and/or stomach, said assembly comprising an elongated relatively soft catheter of a first relatively small diameter and having a length to reach from externally of the patient through the patient's nostril and esophagus and into the patient's intestine and/or stomach, said catheter having an internal bore and a bore outlet adjacent the distal end thereof, and an elongated relatively rigid longitudinally spittable insertion tube of a second and relatively larger diameter having an internal bore receiving and encasing said catheter substantially about the full length thereof, said insertion tube having a length to reach from externally of the patient through the patient's nostril and esophagus and into the patient's intestine and/or stomach, said insertion tube being peripherally continuous but having at least one longitudinal extending line of weakness along the full length thereof whereby said insertion tube is adapted to be split along said line of weakness after insertion of the distal end thereof into the patient for withdrawal and removal of said insertion tube from about said catheter without withdrawal of the distal end of said catheter from the patient's intestines and/or stomach, and catheter fixing means adapted to removably fixed to said catheter adjacent a proximal end thereof externally of the patient for fixedly positioning said catheter during withdrawal and removal of said insertion tube, said catheter fixing means including a generally C-shaped plate means having spaced inner and outer legs, said inner leg adapted to abut the patient adjacent the patient's nostril and having a key-shaped groove having a diameter slightly larger than said second diameter for loosely supporting and guiding said insertion tube and said outer leg having a key-shaped groove of said first diameter for pinching engagement with said catheter to removably fix said catheter to said C-shaped plate means during withdrawal and removal of the insertion tube.

* * * * *